United States Patent
Toth et al.

[11] Patent Number: 6,115,487
[45] Date of Patent: Sep. 5, 2000

[54] CORRECTION ALGORITHM FOR BONE-INDUCED SPECTRAL ARTIFACTS IN COMPUTED TOMOGRAPH IMAGING

[75] Inventors: Thomas L. Toth, Brookfield; Guy M. Besson, Wauwatosa; Jiang Hsieh; Tin-Su Pan, both of Brookfield, all of Wis.

[73] Assignee: General Electric Company, Milwaukee, Wis.

[21] Appl. No.: 09/004,397

[22] Filed: Jan. 8, 1998

[51] Int. Cl.[7] .................................................. G06K 9/00
[52] U.S. Cl. .................................. 382/131; 378/901
[58] Field of Search .................................. 382/131, 260, 382/275; 600/407, 436; 378/4, 18, 21, 24, 26, 901, 207

[56] References Cited

U.S. PATENT DOCUMENTS

| | | | |
|---|---|---|---|
| 4,149,081 | 4/1979 | Seppi | 378/5 |
| 5,235,628 | 8/1993 | Kalender | 378/207 |
| 5,301,108 | 4/1994 | Hsieh | 378/8 |
| 5,530,731 | 6/1996 | Polacin et al. | 378/15 |

*Primary Examiner*—Joseph Mancuso
*Assistant Examiner*—F. E. Cooperrider
*Attorney, Agent, or Firm*—Armstrong Teasdale; Christian G. Cabou; Phyllis Y. Price

[57] ABSTRACT

A spectral correction algorithm for correcting dense object-induced spectral artifacts is described. In one embodiment, a calibration object, representative of typical head scanning conditions is scanned and the data reconstructed to provide an image. A water or water-equivalent cylinder of about the same diameter also is scanned and reconstructed, on the same display field of view (DFOV). These two images are designated respectively by BWEQ and WEQ. The ratio of images BWEQ and WEQ is then evaluated, and a region of interest extracted by multiplying the ratio by a function II(r), to obtain a calibration pattern CP. The calibration pattern is then averaged in azimuth to obtain a calibration vector. This calibration vector is fitted with low—order polynomial, and then divided by the fitting polynomial, to take out from the vector the low frequency components that, for instance, would be introduced on an "ideal" scanner. By subtracting 1.0 from the ratio, and multiplying by a CT number scale factor (ctscale) and an apodizing window Aw(r), a calibration error vector CEV is obtained that is representative of the circularly symmetric image error introduced by the non-corrected bone-induced artifact. The corresponding error calibration vector can be expanded into a circularly symmetric image error pattern I[CEV(r)], and subtracted from the calibration image, to provide a substantially artifact free image. The method can be extended to extract and correlate error vectors on an image segment basis such that the resulting error image pattern is not circularly symmetric.

20 Claims, 2 Drawing Sheets

CORRECTION ALGORITHM FOR BONE-INDUCED SPECTRAL ARTIFACTS IN COMPUTED TOMOGRAPH IMAGING

FIELD OF THE INVENTION

This invention relates generally to computed tomograph (CT) imaging and, more particularly, to a correction algorithm for spectral artifacts induced by dense objects such as bone.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data are processed to construct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

Artifacts may be introduced in CT images when scanning heads and other dense objects. These artifacts, typically limited to the very center of the image where the third generation CT scanner is the most sensitive, are due to beam hardening effects that are not corrected by the water-based beam hardening correction nor by the low-frequency bone-beam hardening correction. Although numerically very small (a fraction of 0.1% in the projection domain), these errors introduce image artifacts.

It would be desirable to eliminate, or substantially reduce, such artifacts. It also would be desirable to eliminate such artifacts without significantly increasing the costs of the system.

SUMMARY OF THE INVENTION

These and other objects may be attained by a bone correction algorithm for correcting bone-induced spectral artifacts. In accordance with one embodiment of the present invention, a calibration object, representative of typical head scanning conditions is scanned and the data reconstructed to provide an image. A water or water-equivalent cylinder of about the same diameter also is scanned and reconstructed, on the same display field of view (DFOV). These two images are designated respectively by BWEQ and WEQ.

The ratio of images BWEQ and WEQ is then evaluated, and a region of interest extracted by multiplying the ratio by a function II(r), to obtain a calibration pattern CP. The calibration pattern is then averaged in azimuth to obtain a calibration vector. This calibration vector is fitted with a low—order polynomial, and then divided by the fitting polynomial, to take out from the vector the low frequency components that, for instance, would be introduced on an "ideal" scanner. By subtracting 1.0 from the ratio, and multiplying by a CT number scale factor (ctscale) and an apodizing window Aw(r), a calibration error vector CEV is obtained that is representative of the circularly symmetric image error introduced by the non-corrected bone-induced artifact. The corresponding error calibration vector can be expanded into a circularly symmetric image error pattern I[CEV(r)], and subtracted from the calibration image, to provide a substantially artifact free image.

For an arbitrary head scan, the steps described above are followed by substituting the scan image SCANI for the calibration image BWEQ, to first obtain a scan pattern SP and then a scan error vector SEV (assuming scaling on the same DFOV). Thresholding the scan pattern SP can be useful in eliminating normal anatomy-related high image-signal variations (such as bone in the region of interest), therefore leading to increased robustness.

The scan error vector can be expanded into a circularly symmetric scan error image pattern, which can be subtracted from the reconstructed scan image to reduce the artifact. Anatomy—dependent structures in the scan data can introduce correct signal contributions into SCANI that are not completely eliminated by azimuthal averaging. By correlating the error vectors CEV and SEV, and subtracting from the scan image the error pattern obtained from the correlation, an anatomical image that is free from dense object-induced spectral artifacts is provided.

For helical scan data acquired on a multislice CT system, different rows contribute with various weights to the projection data that are synthesized before backprojection. As different detector rows might have different sensitivities to bone-induced spectral artifacts, the correction method reflects the combination of various rows via helical weighting. This is accomplished by extending the method described above by considering multislice scans of the calibration phantoms. As those phantoms are designed to be circularly symmetric, the composite calibration image obtained with helical weighting reflects the necessary combination of rows. The calibration object circular symmetry allows generation of a calibration image by using weighted combinations of as many calibration object projections as there are rows in the multislice CT system. The error image from the calibration scan needs to be rotated so that the 'starting angle" reflects that of scan data acquisition. Next, the average over a range of angles is modified so that a number N of angular segments is considered, as determined by the acquisition pitch. Then the procedure above of extracting scan and calibration error vectors is followed for each segment. The final error image to be subtracted is then obtained by blending these multiple correlated scan error vectors into a final image $I[CEV_1, \ldots, CSEV_N]$.

The above described correction algorithm eliminates, or at least substantially reduces, bone-induced spectral artifacts. Such algorithm also does not significantly increase the costs of the system.

DETAILED DESCRIPTION

Figure 1:
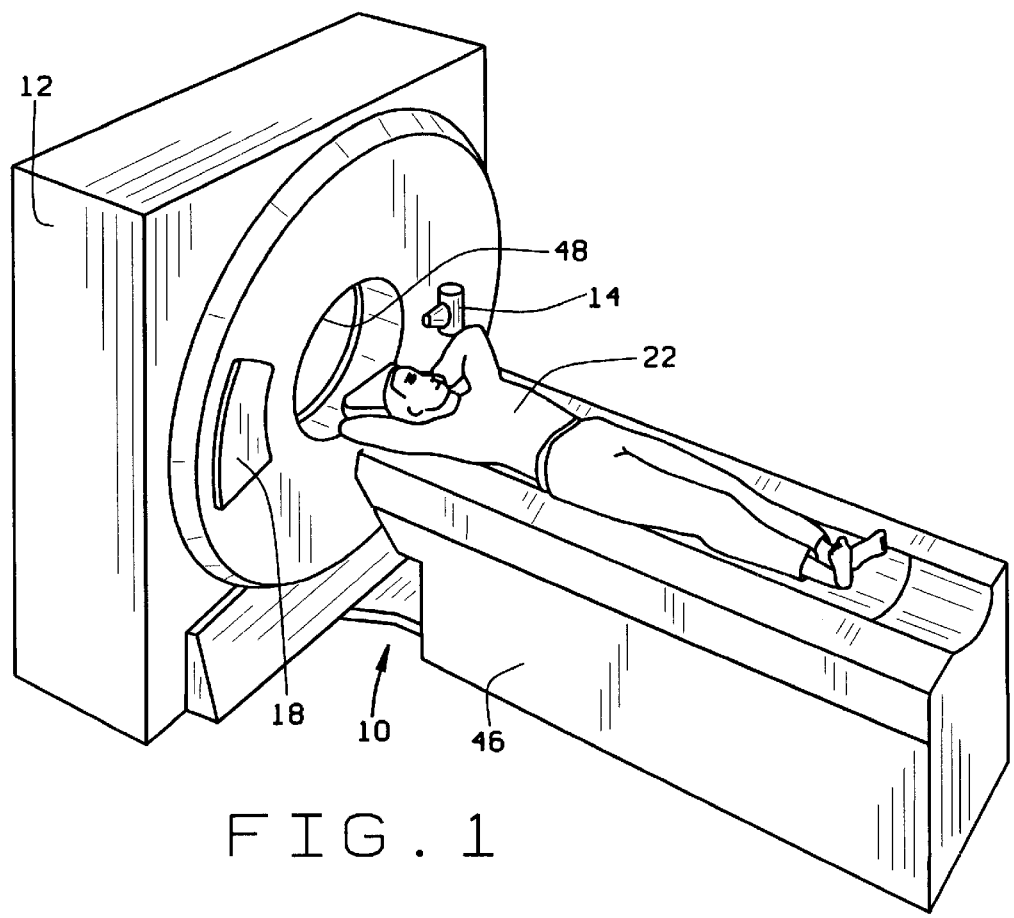
FIG. 1 is a pictorial view of a CT imaging system.
Figure 2:
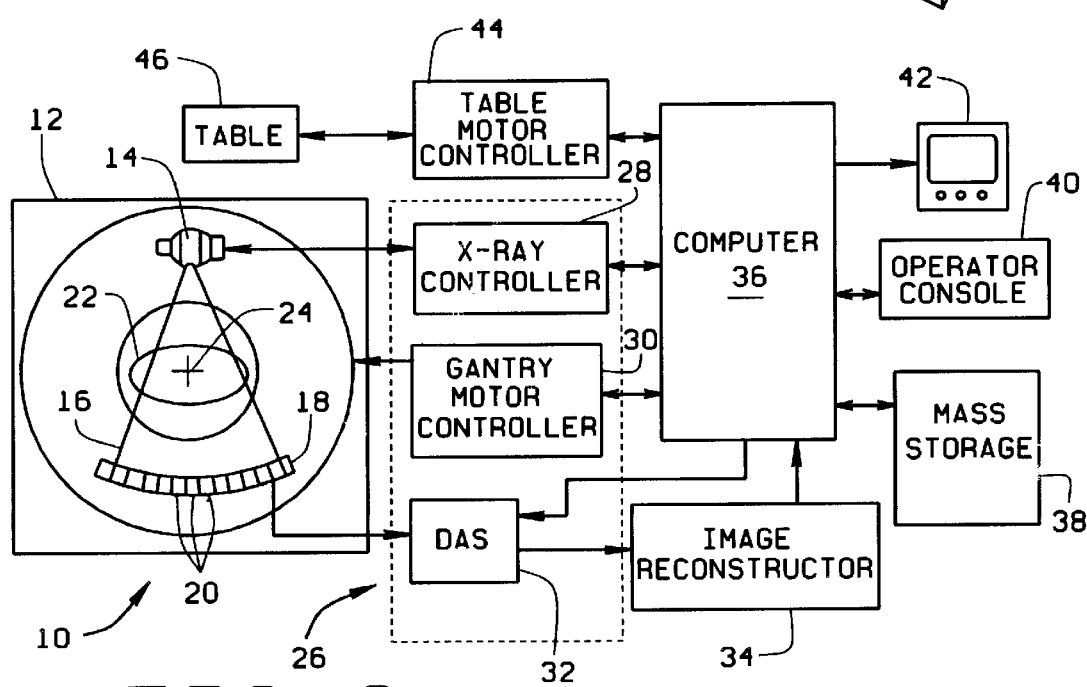
FIG. 2 is a block schematic diagram of the system illustrated in FIG. 1.
Figure 3:
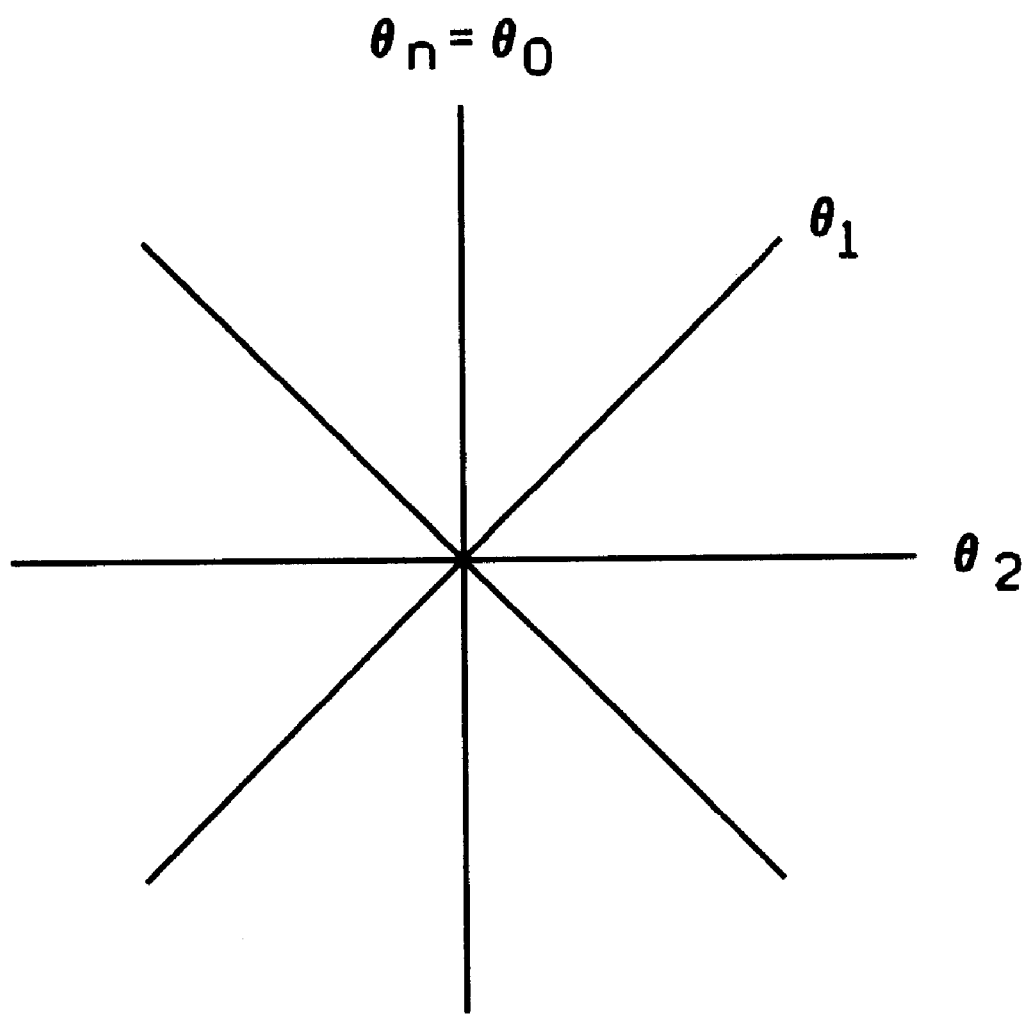
FIG. 3 illustrates image space division used in connection with helical scan data.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The correction algorithm described below may be implemented in computer 36 and practiced using data collected by DAS 32. It will be apparent to those skilled in the art, of course, that such algorithm could be practiced in other components. For example, the algorithm may be practiced directly in image reconstructor 34 so that corrected data is supplied to computer 36. In addition, the correction algorithm is described below as being performed in image space for image quality and computational simplicity. Of course, such correction could be performed on the original data, i.e., projection data images.

In accordance with one embodiment of the present invention, a calibration object, representative of typical head scanning conditions (for example, an 80 mm diameter water equivalent material, with a bone equivalent material ring of about 10 mm thickness) is scanned and the data reconstructed to provide an image. A water or water-equivalent cylinder of about the same diameter also is scanned and reconstructed, on the same display field of view (DFOV). These two images are designated respectively by BWEQ and WEQ.

Other calibration phantoms can, of course, be used. For example, a flat filter formed by a combination of Titanium and Plexiglas may be effective in identifying the detector sensitivity. Such a filter could be mounted close to the source collimator to provide the option of automatic detector monitoring. This sensitivity can then be used as projection data to produce an image error pattern analogous to I[CEV(r)] described below. In another example, detector sensitivities may be extracted by using combinations of Aluminum and flexiglass object phantoms.

The ratio of images BWEQ and WEQ is then evaluated, and a region of interest extracted by multiplying the ratio by a function II(r), to obtain a calibration pattern CP.

$$CP(r, \theta) = II(r) \times \frac{BWEQ(r, \theta)}{WEQ(r, \theta)} \quad (1)$$

where (with R being the radius of the region of interest):

$$II(r) = 1.0, r < |R|, 0 \text{ else.} \quad (2)$$

Of course, similar approaches would yield very similar results. For example, in equation (1) the water equivalent phantom could be replaced by a water phantom. Also, the calibration pattern CP could be written as:

$$CP(r, \theta) = II(r) \times \frac{BWEQ(r, \theta) - WEQ(r, \theta)}{WEQ(r, \theta)} \quad (3)$$

The calibration pattern is then averaged in azimuth to obtain a calibration vector:

$$CV(r) = \int_0^{2\pi} CP(r, \theta) d\theta \quad (4)$$

The calibration vector is fitted with low—order polynomial, and then divided by the fitting polynomial, to take out from the vector the low frequency components (that for instance would be introduced on an "ideal" scanner by the ratio defined in Equation (1). By subtracting 1.0 from the ratio, and multiplying by a CT number scale factor (ctscale, where a "CT number scale factor" is a scale factor normalizing CT numbers to the attenuation of water, which has a scaled CT number of 1000) and an apodizing window Aw(r) (where an "apodizing window" is a weighting function or filter designed to limit the range of a function and generally to provide a smooth transition to an end range), a calibration error vector CEV is obtained that is representative of the circularly symmetric image error introduced by the non-corrected bone-induced artifact:

$$CEV(r) = ctscale \times Aw(r) \times \left\{ \frac{CV(r)}{Polynomial\_Fit[CV(r)]} - 1.0 \right\} \quad (5)$$

The corresponding error calibration vector can be expanded into a circularly symmetric image error pattern I[CEV(r)], and subtracted from the calibration image, to provide a substantially artifact free image.

For an arbitrary head scan, the steps in equations (1) to (3) are followed by substituting the scan image SCANI:

$$SP(r, \theta) = II(r) \times \frac{SCANI(r, \theta)}{WEQ(r, \theta)} \quad (6)$$

for the calibration image BWEQ, to first obtain a scan pattern SP and then a scan error vector SEV (assuming scaling on the same DFOV):

$$SEV(r) = ctscale \times Aw(r) \times \left\{ \frac{SV(r)}{Polynomial\_Fit[SV(r)]} - 1.0 \right\} \quad (7)$$

Thresholding the scan pattern SP can be useful in eliminating normal anatomy-related high image-signal variations (such as bone in the region of interest), therefore leading to increased robustness.

The scan error vector can be expanded into a circularly symmetric scan error image pattern, which can be subtracted from the reconstructed scan image to reduce the artifact. Anatomy—dependent structures in the scan data can introduce correct signal contributions into SCANI that are not completely eliminated by azimuthal averaging. By correlating the error vectors CEV and SEV, and subtracting from the scan image the error pattern obtained from the correlation the following is provided:

$$I[CSEV(r)]; CSEV(r) = Correlation(SEV, CEV) \times SEV(r) \quad (8)$$

The correlation may be modelled by a low order polynomial, and computed via a least-squares method (for instance, using the singular value decomposition method). A simple threshold can also be employed. If the correlation between SEV and CEV falls below the threshold, no correction would be performed. The correlation polynomial can be calculated over a number of sub-segments of the vectors, thereby increasing the degrees of freedom without introducing instabilities.

A number of approaches for extracting the error term from the vectors can be used with similar results. For instance, instead of fitting the vector with a polynomial and subtracting 1.0, the vector can be convolved with an appropriately tailored filtering kernel. Similarly, and to improve on the method to correct image errors that are not circularly symmetric, Equation (3) could be replaced by:

$$CV_1(r) = \int_{\theta_0}^{\theta_1} CP(r, \theta) d\theta; \quad (9)$$

$$CV_2(r) = \int_{\theta_1}^{\theta_2} CP(r, \theta) d\theta, \ldots, CV_n(r) = \int_{\theta_{N_1}}^{\theta_N} CP(r, \theta) d\theta.$$

where N angular segments are considered and:

$$\theta_N - \theta_0 = 2\pi \quad (10)$$

For each segment, processing in accordance with Equations 5 and 7 would take place, and the final error image would be composed from the corresponding (blended via feathering at the segment interfaces) "error image segments."

For helical scan data acquired on a multislice CT system, different rows contribute with various weights to the projection data that are synthesized before backprojection. As different detector rows might have different sensitivities to bone-induced spectral artifacts, the correction method reflects the combination of various rows via helical weighting. This is accomplished by extending the method described above by considering multislice scans of the calibration phantoms. As those phantoms are designed to be circularly symmetric, the composite calibration image reflects the necessary combination of rows via the helical weights. The circular symmetry allows generation of a calibration image by using weighted combinations of as many calibration object projections as there are rows in the multislice CT system. The error image from the calibration scan needs to be rotated so that the 'starting angle" reflects that of scan data acquisition. Next, the average over a range of angles is modified so that a number N of angular segments is considered, as determined by the acquisition pitch. Then the procedure above of extracting scan and calibration error vectors is followed for each segment. The final error image to be subtracted is then obtained by blending these multiple correlated scan error vectors into a final helical image IH[CSHEV(r)] where:

$$CSHEV(r) = Correlation\left( \sum_{i=1}^{N} w_i CEV_i(r), SHEV(r) \right) \times SHEV(r) \quad (11)$$

As explained above, the above described correction algorithms can be applied to projection data. With projection data, views are averaged for a given angular range, and the ratio of the Bone calibration object (or scan object) to a WEQ calibration object is determined, in accordance with Equation (1), and error estimation proceeds as in Equations (2)–(7). The error thus extracted can be used to either correct the scan data directly (therefore bypassing the need for image post-processing), or to define an error image via subsequent filtering and backprojection. The image correction algorithm also can be applied to other artifact correction, such as for instance Z-slope correction. Of course the calibration phantom selected to extract the system sensitivity may vary depending upon the correction being performed.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for correcting an image having dense object-induced spectral artifacts generated using data collected in a computed tomography system, said method comprising the steps of:
   (a) reconstructing an image BWEQ of a calibration object;
   (b) reconstructing an image WEQ of a water equivalent cylinder having about a same diameter as the calibration object;
   (c) generating a ratio of images BWEQ and WEQ;
   (d) extracting a region of interest by multiplying the generated ratio by a function II(r) to obtain a calibration pattern CP;
   (e) averaging the calibration pattern in azimuth to obtain a calibration vector;
   (f) removing low frequency components from the vector;
   (g) multiplying the result of step (f) by a CT number scale factor (ctscale) and an apodizing window Aw(r) to generate a calibration error vector CEV representative of an image error introduced by the non-corrected dense object-induced artifact.

2. A method in accordance with claim 1 wherein removing low frequency components from the vector comprises the steps of:
fitting the calibration vector with low—order polynomial; and
dividing the fitting polynomial to remove low frequency.

3. A method in accordance with claim 1 further comprising the step of expanding the calibration error vector into an image error pattern I[CEV(r)], and subtracting the image error pattern from the calibration image to provide a substantially artifact free image.

4. A method in accordance with claim 1 wherein the calibration object is a water equivalent material with a bone equivalent material ring.

5. A method in accordance with claim 1 wherein the calibration object includes material selected from at least one of Titanium, Plexiglass, and aluminum.

6. A method for correcting an image of a head having dense object-induced spectral artifacts generated using data collected in a computed tomography system, said method comprising the steps of:
(a) reconstructing a scan image SCANI of the head;
(b) reconstructing an image WEQ1 of a water equivalent cylinder having about a same diameter as the head;
(c) generating a ratio of images SCANI and WEQ1;
(d) extracting a region of interest by multiplying the generated ratio of SCANI and WEQ1 by a function II(r) to obtain a scan pattern SP;
(e) averaging the scan pattern in azimuth to obtain a scan vector;
(f) removing low frequency components from the scan vector; and
(g) multiplying the result of said step of removing low frequency components from the scan vector by a CT number scale factor (ctscale) and an apodizing window Aw(r) to generate a scan error vector SEV representative of an image error introduced by non-corrected bone-induced artifact.

7. A method in accordance with claim 6 wherein removing low frequency components from the vector comprises the steps of:
fitting the calibration vector with low—order polynomial; and
dividing the fitting polynomial to remove low frequency.

8. A method in accordance with claim 6 further comprising the steps of:
determining a calibration error vector CEV using a calibration object, and
correlating CEV and SEV, and blending the resulting CSEVi by feathering at segment interfaces to generate an error image.

9. A method in accordance with claim 8 further comprising the step of subtracting the error image from the calibration image to provide a substantially artifact free image.

10. A method in accordance with claim 6 further comprising the steps of generating calibration and scan error vectors for each detector row, correlating the calibration and scan error vectors for each row, and determining a final error image as a function of a plurality of correlated said scan error vectors.

11. A method in accordance with claim 10 wherein each row scan error vector is calculated over an angular segment based on a particular image plane to be reconstructed.

12. A method in accordance with claim 8 wherein determining a calibration error vector CEV using a calibration object comprises the steps of:
reconstructing an image BWEQ of a calibration object;
reconstructing an image WEQ2 of a water equivalent cylinder having about a same diameter as the calibration object;
generating a ratio of images BWEQ and WEQ2;
extracting a region of interest by multiplying the generated ratio of BWEQ and WEQ2 by function II(r) to obtain a calibration pattern CP;
averaging the calibration pattern CP in azimuth to obtain a calibration vector;
removing low frequency components from the calibration vector; and
multiplying the result of said step of removing low frequency components from the calibration vector by a CT number scale factor (ctscale) and an apodizing window Aw(r) to generate a calibration error vector CEV representative of an image error introduced by a non-corrected dense object-induced artifact.

13. An apparatus for correcting an image having dense object-induced spectral artifacts generated using data collected in a computed tomography system, said apparatus configured to:
(a) reconstruct an image BWEQ of a calibration object;
(b) reconstruct an image WEQ of a water equivalent cylinder having about a same diameter as the calibration object;
(c) generate a ratio of images BWEQ and WEQ;
(d) extract a region of interest by multiplying the generated ratio by a function II(r) to obtain a calibration pattern CP;
(e) average the calibration pattern in azimuth to obtain a calibration vector;
(f) remove low frequency components from the vector;
(g) multiply the result of step (f) by a CT number scale factor (ctscale) and an apodizing window Aw(r) to generate a calibration error vector CEV representative of an image error introduced by the non-corrected dense object-induced artifact.

14. An apparatus in accordance with claim 13 wherein said apparatus being configured to remove low frequency components from the vector comprises said apparatus being configured to:
fit the calibration vector with a low—order polynomial; and
divide the fitting polynomial to remove low frequencies.

15. An apparatus in accordance with claim 13 further configured to expand the calibration error vector into an image error pattern I, and to subtract the image error pattern from the calibration image to provide a substantially artifact free image.

16. An apparatus for correcting an image of a head having dense object-induced spectral artifacts generated using data collected in a computed tomography system, said apparatus configured to:
(a) reconstruct a scan image SCANI of the head;
(b) reconstruct an image WEQ1 of a water equivalent cylinder having about the same diameter as the head;
(c) generate a ratio of images SCANI and WEQ1;
(d) extract a region of interest by multiplying the generated ratio of SCANI and WEQ1 by a function II(r) to obtain a scan pattern SP;

(e) average the scan pattern in azimuth to obtain a scan vector;

(f) remove low frequency components from the scan vector; and (g) multiply the result of said step of removing low frequency components from the scan vector by a CT number scale factor (ctscale) and an apodizing window Aw(r) to generate a scan error vector SEV representative of an image error introduced by non-corrected bone-induced artifact.

17. An apparatus in accordance with claim 16 wherein said apparatus being configured to remove low frequency components from the vector comprises said apparatus being configured to:

fit the calibration vector with a low—order polynomial; and divide the fitting polynomial to remove low frequency.

18. An apparatus in accordance with claim 16 further configured to:

determine a calibration error vector CEV using a calibration object, and correlate CEV and SEV, and blend the resulting CSEVi by feathering at segment interfaces to generate an error image.

19. An apparatus in accordance with claim 18 further configured to subtract the error image from the calibration image to provide a substantially artifact free image.

20. An apparatus in accordance with claim 16 further configured to generate calibration and scan error vectors for each detector row, correlate the calibration and scan error vectors for each row, and determine a final error image as a function of a plurality of correlated said scan error vectors.

* * * * *